United States Patent
Shiomi et al.

(10) Patent No.: US 7,342,116 B2
(45) Date of Patent: Mar. 11, 2008

(54) PROCESS FOR PRODUCING HETEROCYCLIC ALDEHYDE

(75) Inventors: Yasuhiro Shiomi, Osaka (JP); Osamu Uno, Osaka (JP); Akio Ohta, Osaka (JP); Takeshi Sunakami, Tokyo (JP)

(73) Assignee: Koei Chemical Co., Ltd., Osaka-Shi (JP)

( * ) Notice: Subject to any disclaimer, the term of this patent is extended or adjusted under 35 U.S.C. 154(b) by 476 days.

(21) Appl. No.: 10/509,228

(22) PCT Filed: Mar. 25, 2003

(86) PCT No.: PCT/JP03/03568

§ 371 (c)(1),
(2), (4) Date: Sep. 24, 2004

(87) PCT Pub. No.: WO03/080575

PCT Pub. Date: Oct. 2, 2003

(65) Prior Publication Data

US 2005/0124807 A1    Jun. 9, 2005

(30) Foreign Application Priority Data

Mar. 26, 2002 (JP) ............................. 2002-086974

(51) Int. Cl.
*C07D 211/70* (2006.01)
*C07D 333/22* (2006.01)

(52) U.S. Cl. .................. 546/314; 546/315; 549/70
(58) Field of Classification Search ........... 549/70; 546/314, 315
See application file for complete search history.

(56) References Cited

U.S. PATENT DOCUMENTS

2002/0035223 A1    3/2002    Burkhardt et al.

FOREIGN PATENT DOCUMENTS

| EP | 316783 A1 | 5/1989 |
| EP | 1 103 537 A1 | 5/2001 |
| JP | 2002-145928 | 5/2002 |

OTHER PUBLICATIONS

Inokuchi et. al., "A Selective and Efficient Method for Alcohol Oxidations Mediated by N-Oxoammonium Salts in Combination with Sodium Bromite", J. Org. Chem. 1990, 55, 462-466.*

(Continued)

*Primary Examiner*—Janet L. Andres
*Assistant Examiner*—Binta Robinson
(74) *Attorney, Agent, or Firm*—Antonelli, Terry, Stout & Kraus, LLP.

(57) ABSTRACT

A process is disclosed for preparing a heterocyclic aldehyde by oxidizing a heterocyclic alcohol with high selectivity and high yield. Specifically, the heterocyclic aldehyde is prepared by reacting a heterocyclic compound having at least one hydroxymethyl group bonded to a carbon atom of a heterocyclic ring with a hypohalogenous acid salt in the presence of a base to oxidize the hydroxymethyl group, wherein reaction is conducted in the co-presence of a 2,2,6,6-tetramethylpiperidine-1-oxyl derivative having at least two 2,2,6,6-tetramethylpiperidine-1-oxyl-4-yl groups.

2 Claims, 4 Drawing Sheets

OTHER PUBLICATIONS

Inokuchi et. al., "A New Oxidizing System for Aromatic Alcohols by the Combination of N-Oxoammonium Salt and Electrosynthesized Tetraalkylammonium Tribromide", Bull. Chem. Soc. Jpn., 64, 796-800 (1991), vol. 64, No. 3.*

Sourkounl-A., G., Kirschning, A., A New Polymer-Attached Reagent for the Oxidation of Primary and Secondary Alcohols; Organic Letters, 2000, vol. 2, No. 24, pp. 3781 to 3784.

Sourkouni-A., G., Kirschning, A., A New Polymer-Attached Reagent for the Oxidation of Primary and Secondary Alcohols; Organic Letters, 2000, vol. 2, No. 24, pp. 3781 to 3784.

Weik, S., Nicholson, G., Gunther, J., Rademann, J., Oxoammonium Resins as Metal-Free, Highly Reactive, Versatile Polymeric Oxidation Reagents. Angew. Chem. Int. Ed., 2001, vol. 40, No. 8, pp. 1436 to 1439.

* cited by examiner

PROCESS FOR PRODUCING HETEROCYCLIC ALDEHYDE

RELATED APPLICATIONS

This is a U.S. national phase application filed under 35 U.S.C. §371 of International Application No. PCT/JP2003/03568 filed Mar. 25, 2003, which claims priority of Japanese Application No. 2002-86974 filed Mar. 26, 2002.

TECHNICAL FIELD

The present invention relates to a process for preparing heterocyclic aldehyde by oxidizing a heterocyclic compound having at least one hydroxymethyl group bonded to a carbon atom of a heterocyclic ring (hereinafter referred to as heterocyclic alcohol).

BACKGROUND ART

As a method for preparing a heterocyclic aldehyde by oxidizing a heterocyclic alcohol, known is the method of preparing 3-pyridinecarbaldehyde or 4-pyridinecarbaldehyde by oxidizing 3-pyridinemethanol or 4-pyridinemethanol with sodium hypochlorite in the presence of a base and 2,2,6,6-tetramethylpiperidine-1-oxyl (see European Patent Publication No. 316783 and Org. Synth., 69, 212 (1990)).

Based on the above conventional method, the present inventors have studied the method of preparing a heterocyclic aldehyde by oxidizing a heterocyclic alcohol with hypohalogenous acid salt in the presence of a base and 2,2,6,6-tetramethylpiperidine-1-oxyl. As a result, as described below in Comparative Examples, the desired heterocyclic aldehyde is oxidized further and the selectivity and yield of the desired heterocyclic aldehyde is not satisfactory, as heterocyclic carboxylic acid is by-produced.

The present invention aims to provide a process for preparing a heterocyclic aldehyde by oxidizing a heterocyclic alcohol with high selectivity and high yield.

DISCLOSURE OF INVENTION

As a result of intensive studies to solve the above problems, the present inventors have found that when preparing a heterocyclic aldehyde by oxidizing a heterocyclic alcohol with hypohalogenous acid salt in the presence of a base, side reactions can be prevented and the desired heterocyclic aldehyde can be prepared with high selectivity and high yield, in the case that a 2,2,6,6-tetramethylpiperidine-1-oxyl derivative having at least two 2,2,6,6-tetramethylpiperidine-1-oxyl-4-yl groups is used instead of 2,2,6,6-tetramethylpiperidine-1-oxyl. Thus, the present invention was achieved.

That is, the present invention relates to a process for preparing a heterocyclic aldehyde, which comprises reacting a heterocyclic alcohol with a hypohalogenous acid salt in the presence of a base to oxidize the hydroxymethyl group, wherein the reaction is conducted in the co-presence of a 2,2,6,6-tetramethylpiperidine-1-oxyl derivative having at least two 2,2,6,6-tetramethylpiperidine-1-oxyl-4-yl groups.

BEST MODE FOR CARRYING OUT THE INVENTION

Figure 1:
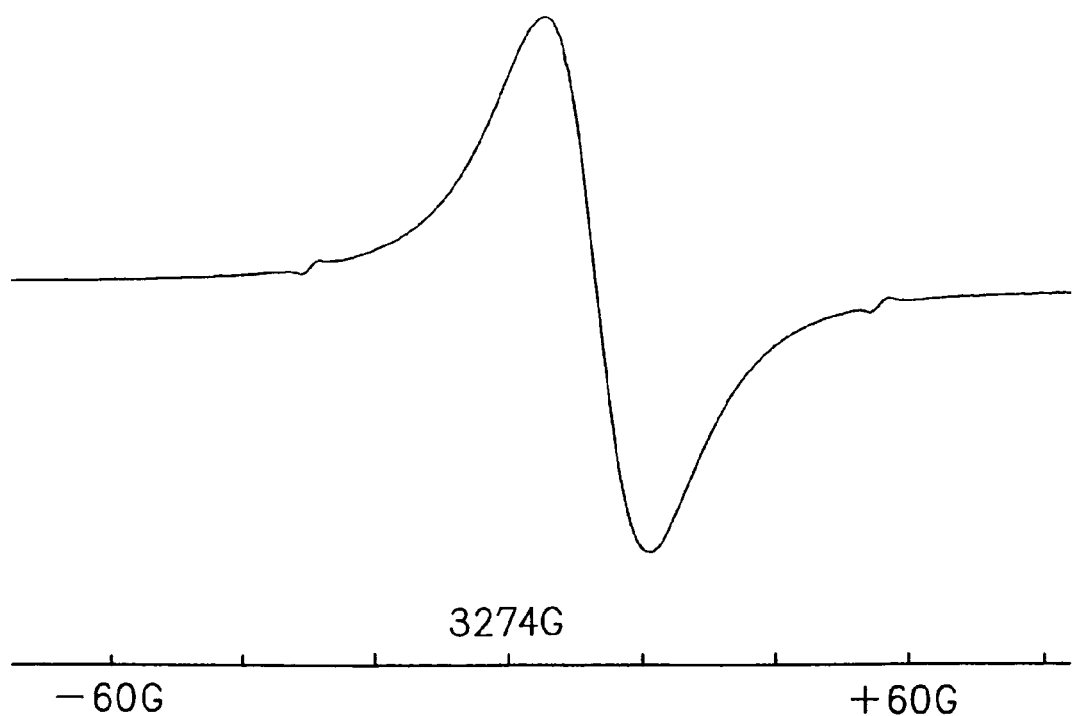
FIG. 1 is an ESR chart of compound (14) obtained in Reference Example 3.

The present invention is described in detail below.

Examples of the heterocyclic ring in the heterocyclic alcohol used in the present invention are 5 to 6 membered heteroaromatic rings having 1 to 3 hetero atoms selected from the group consisting of nitrogen atoms, sulfur atoms and oxygen atoms as the constituent atoms of the ring. A heteroaromatic ring or thiophene ring having 1 to 3 nitrogen atoms as the constituent atoms of the ring is preferable and a pyridine ring, a pyridazine ring, a pyrimidine ring, a pyrazine ring and a thiophene ring are more preferable. Also, besides having at least one hydroxymethyl group bonded to a carbon atom of the ring, the heterocyclic alcohol of the present invention can have at least one substituent that is inert to the oxidization reaction of the present invention. Examples of the substituent that is inert to the oxidization reaction of the present invention are an alkyl group, a cycloalkyl group, an aralkyl group, an aryl group, an alkoxy group, a nitro group, a hydroxy group and a halogen atom.

A preferable heterocyclic alcohol is a heterocyclic compound represented by formula (1):

(1)

(wherein Q represents a pyridine ring, a pyridazine ring, a pyrimidine ring, a pyrazine ring or a thiophene ring; CH$_2$OH and R$^1$ are substituents bonded to a carbon atom of a pyridine ring, a pyridazine ring, a pyrimidine ring, a pyrazine ring or a thiophene ring; R$^1$ represents an alkyl group, a cycloalkyl group, an aralkyl group, an aryl group, an alkoxy group, a nitro group, a hydroxy group or a halogen atom; j is an integer of 0 to 4 when Q is a pyridine ring, or an integer of 0 to 3 when Q is a pyridazine ring, a pyrimidine ring, a pyrazine ring or a thiophene ring).

In the above formula (1), examples of the alkyl group represented by R$^1$ are linear or branched alkyl groups having 1 to 6 carbon atoms, preferably a methyl group or an ethyl group. Examples of the cycloalkyl group are cycloalkyl groups having 3 to 8 carbon atoms, preferably a cyclopentyl group, a cyclohexyl group or a cycloheptyl group. Examples of the aralkyl group are benzyl groups and phenetyl groups, wherein a benzene ring can have at least one substituent that is inert to the reaction of the present invention such as an alkyl group including a methyl group and an ethyl group, preferably a benzyl group. Examples of the aryl group are phenyl groups, naphthyl groups and pyridyl groups, wherein an aromatic ring can have at least one substituent that is inert to the reaction of the present invention such as an alkyl group including a methyl group and an ethyl group, preferably a phenyl group. Examples of the alkoxy group are linear or branched alkoxy groups having 1 to 6 carbon atoms, preferably a methoxy group or an ethoxy group. When j in the formula is an integer of 2 or larger, the plural R$^1$ can respectively be the same or different substituents.

More preferable heterocyclic alcohols are pyridinemethanols represented by formula (3):

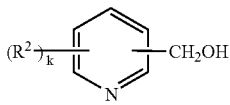

(wherein CH₂OH and R² are substituents bonded to a carbon atom of a pyridine ring; R² represents an alkyl group, a cycloalkyl group, an aralkyl group, an aryl group, an alkoxy group, a nitro group, a hydroxy group or a halogen atom; k is an integer of 0 to 4) and thiophenemethanols represented by formula (5):

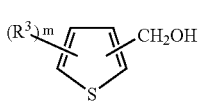

(wherein CH₂OH and R³ are substituents bonded to a carbon atom of a thiophene ring; R³ represents an alkyl group, a cycloalkyl group, an aralkyl group, an aryl group, an alkoxy group, a nitro group, a hydroxy group or a halogen atom; m is an integer of 0 to 3). Particularly preferable heterocyclic alcohols are pyridinemethanols shown in formula (3), wherein R² is an alkyl group and k is an integer of 0 to 4, and thiophenemethanols shown in formula (5), wherein R³ is an alkyl group and m is an integer of 0 to 3.

In formula (3), the alkyl group, the aralkyl group, the aryl group, the alkoxy group and the halogen atom represented by R² are the same as those represented by R¹ in the above formula (1). When k in the formula is an integer of 2 or larger, the plural R² can respectively be the same or different substituents.

Specific examples of the compound that can suitably be used in the present invention as the heterocyclic alcohol represented by the above formula (3) are 2-pyridinemethanol, 3-methyl-2-pyridinemethanol, 4-methyl-2-pyridinemethanol, 5-methyl-2-pyridinemethanol, 6-methyl-2-pyridinemethanol, 3-ethyl-2-pyridinemethanol, 4-ethyl-2-pyridinemethanol, 5-ethyl-2-pyridinemethanol, 6-ethyl-2-pyridinemethanol, 3-n-propyl-2-pyridinemethanol, 4-n-propyl-2-pyridinemethanol, 5-n-propyl-2-pyridinemethanol, 6-n-propyl-2-pyridinemethanol, 3-isopropyl-2-pyridinemethanol, 4-isopropyl-2-pyridinemethanol, 5-isopropyl-2-pyridinemethanol, 6-isopropyl-2-pyridinemethanol, 3-benzyl-2-pyridinemethanol, 4-benzyl-2-pyridinemethanol, 5-benzyl-2-pyridinemethanol, 6-benzyl-2-pyridinemethanol, 3-phenyl-2-pyridinemethanol, 4-phenyl-2-pyridinemethanol, 5-phenyl-2-pyridinemethanol, 6-phenyl-2-pyridinemethanol, 3-methoxy-2-pyridinemethanol, 4-methoxy-2-pyridinemethanol, 5-methoxy-2-pyridinemethanol, 6-methoxy-2-pyridinemethanol, 3-nitro-2-pyridinemethanol, 4-nitro-2-pyridinemethanol, 5-nitro-2-pyridinemethanol, 6-nitro-2-pyridinemethanol, 3-hydroxy-2-pyridinemethanol, 4-hydroxy-2-pyridinemethanol, 5-hydroxy-2-pyridinemethanol, 6-hydroxy-2-pyridinemethanol, 3-chloro-2-pyridinemethanol, 4-chloro-2-pyridinemethanol, 5-chloro-2-pyridinemethanol, 6-chloro-2-pyridinemethanol, 3-pyridinemethanol, 2-methyl-3-pyridinemethanol, 4-methyl-3-pyridinemethanol, 5-methyl-3-pyridinemethanol, 6-methyl-3-pyridinemethanol, 2-ethyl-3-pyridinemethanol, 4-ethyl-3-pyridinemethanol, 5-ethyl-3-pyridinemethanol, 6-ethyl-3-pyridinemethanol, 2-n-propyl-3-pyridinemethanol, 4-n-propyl-3-pyridinemethanol, 5-n-propyl-3-pyridinemethanol, 6-n-propyl-3-pyridinemethanol, 2-isopropyl-3-pyridinemethanol, 4-isopropyl-3-pyridinemethanol, 5-isopropyl-3-pyridinemethanol, 6-isopropyl-3-pyridinemethanol, 2-benzyl-3-pyridinemethanol, 4-benzyl-3-pyridinemethanol, 5-benzyl-3-pyridinemethanol, 6-benzyl-3-pyridinemethanol, 2-phenyl-3-pyridinemethanol, 4-phenyl-3-pyridinemethanol, 5-phenyl-3-pyridinemethanol, 6-phenyl-3-pyridinemethanol, 2-methoxy-3-pyridinemethanol, 4-methoxy-3-pyridinemethanol, 5-methoxy-3-pyridinemethanol, 6-methoxy-3-pyridinemethanol, 2-nitro-3-pyridinemethanol, 4-nitro-3-pyridinemethanol, 5-nitro-3-pyridinemethanol, 6-nitro-3-pyridinemethanol, 2-hydroxy-3-pyridinemethanol, 4-hydroxy-3-pyridinemethanol, 5-hydroxy-3-pyridinemethanol, 6-hydroxy-3-pyridinemethanol, 2-chloro-3-pyridinemethanol, 4-chloro-3-pyridinemethanol, 5-chloro-3-pyridinemethanol, 6-chloro-3-pyridinemethanol, 4-pyridinemethanol, 2-methyl-4-pyridinemethanol, 3-methyl-4-pyridinemethanol, 2-ethyl-4-pyridinemethanol, 3-ethyl-4-pyridinemethanol, 2-n-propyl-4-pyridinemethanol, 3-n-propyl-4-pyridinemethanol, 2-isopropyl-4-pyridinemethanol, 3-isopropyl-4-pyridinemethanol, 2-benzyl-4-pyridinemethanol, 3-benzyl-4-pyridinemethanol, 2-phenyl-4-pyridinemethanol, 3-phenyl-4-pyridinemethanol, 2-methoxy-4-pyridinemethanol, 3-methoxy-4-pyridinemethanol, 2-nitro-4-pyridinemethanol, 3-nitro-4-pyridinemethanol, 2-hydroxy-4-pyridinemethanol, 3-hydroxy-4-pyridinemethanol, 2-chloro-4-pyridinemethanol and 3-chloro-4-pyridinemethanol.

In formula (5), the alkyl group, the aralkyl group, the aryl group, the alkoxy group and the halogen atom represented by R³ are the same as those represented by R¹ in the above formula (1). When m in the formula is an integer of 2 or larger, the plural R³ can respectively be the same or different substituents.

Specific examples of the compound that can suitably be used in the present invention as the heterocyclic alcohol represented by the above formula (5) are 2-thiophenemethanol, 3-methyl-2-thiophenemethanol, 4-methyl-2-thiophenemethanol, 5-methyl-2-thiophenemethanol, 3-ethyl-2-thiophenemethanol, 4-ethyl-2-thiophenemethanol, 5-ethyl-2-thiophenemethanol, 3-n-propyl-2-thiophenemethanol, 4-n-propyl-2-thiophenemethanol, 5-n-propyl-2-thiophenemethanol, 3-isopropyl-2-thiophenemethanol, 4-isopropyl-2-thiophenemethanol, 5-isopropyl-2-thiophenemethanol, 3-benzyl-2-thiophenemethanol, 4-benzyl-2-thiophenemethanol, 5-benzyl-2-thiophenemethanol, 3-phenyl-2-thiophenemethanol, 4-phenyl-2-thiophenemethanol, 5-phenyl-2-thiophenemethanol, 3-methoxy-2-thiophenemethanol, 4-methoxy-2-thiophenemethanol, 5-methoxy-2-thiophenemethanol, 3-nitro-2-thiophenemethanol, 4-nitro-2-thiophenemethanol, 5-nitro-2-thiophenemethanol, 3-hydroxy-2-thiophenemethanol, 4-hydroxy-2-thiophenemethanol, 5-hydroxy-2-thiophenemethanol, 3-chloro-2-thiophenemethanol, 4-chloro-2-thiophenemethanol, 5-chloro-2-thiophenemethanol, 3-thiophenemethanol, 2-methyl-3-thiophenemethanol, 4-methyl-3-thiophenemethanol, 5-methyl-3-thiophenemethanol, 2-ethyl-3-thiophenemethanol, 4-ethyl-3-thiophenemethanol, 5-ethyl-3-thiophenemethanol, 2-n-propyl-3-thiophenemethanol, 4-n-propyl-3-thiophenemethanol, 5-n-propyl-3-thiophenemethanol, 2-isopropyl-3-thiophenemethanol, 4-isopropyl-3-thiophenemethanol, 5-isopropyl-3-thiophenemethanol, 2-benzyl-3-thiophenemethanol, 4-benzyl-3-thiophenemethanol, 5-benzyl-3-thiophenemethanol, 2-phenyl-3-thiophenemethanol, 4-phenyl-3-thiophenemethanol, 5-phenyl-3-thiophenemethanol, 2-methoxy-3-thiophenemethanol, 4-methoxy-3-thiophenemethanol, 5-methoxy-3-thiophenemethanol, 2-nitro-3-thiophenemethanol, 4-nitro-3-thiophenemethanol, 5-nitro-3-thiophenemethanol, 2-hydroxy-3-thiophenemethanol, 4-hydroxy-3-thiophenemethanol, 5-hydroxy-3-thiophenemethanol, 2-chloro-3-thiophenemethanol, 4-chloro-3-thiophenemethanol and 5-chloro-3-thiophenemethanol.

By the oxidization reaction of the present invention, a heterocyclic aldehyde that corresponds to the heterocyclic alcohol used in the reaction is prepared, wherein the hydroxymethyl group thereof is converted into a formyl group. For example, from the heterocyclic compound represented by formula (1), a heterocyclic aldehyde represented by formula (2):

$(R^1)_j$Q-CHO  (2)

(wherein Q, $R^1$ and j are the same as above), wherein the hydroxymethyl group in the molecule is converted into a formyl group, is prepared. From pyridinemethanols represented by formula (3), pyridinecarbaldehydes represented by formula (4):

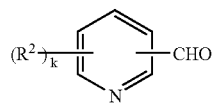

(4)

(wherein $R^2$ and k are the same as above), wherein the hydroxymethyl group in the molecule of the pyridinemethanols is converted into a formyl group, are prepared.

Also, from thiophenemethanols represented by formula (5), thiophenecarbaldehydes represented by formula (6):

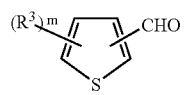

(6)

(wherein $R^3$ and m are the same as above), wherein the hydroxymethyl group in the molecule of the thiophenemethanols are converted into a formyl group, are prepared.

In the present invention, it is important to use a 2,2,6,6-tetramethylpiperidine-1-oxyl derivative having at least two, preferably at least four, 2,2,6,6-tetramethylpiperidine-1-oxyl-4-yl groups, that is a group represented by the following formula:

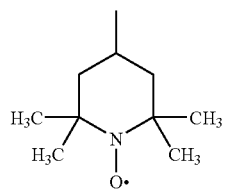

in the oxidization reaction of the heterocyclic alcohol. By conducting oxidization reaction using such 2,2,6,6-tetramethylpiperidine-1-oxyl derivatives, side reactions can be inhibited and heterocyclic aldehyde can be prepared selectively with high yield.

Examples of the organic compound having at least two 2,2,6,6-tetramethylpiperidine-1-oxyl-4-yl groups are compounds, which are obtained by oxidizing a compound having at least two 2,2,6,6-tetramethyl-4-piperidyl groups, selected from hindered amine light stabilizers (HALS) known as plastic additives, to convert the 2,2,6,6-tetramethyl-4-piperidyl groups into 2,2,6,6-tetramethylpiperidine-1-oxyl-4-yl groups, by a known method for preparing imine-N-oxyl from imine.

Specific examples are a compound represented by formula (7) [hereinafter referred to as compound (7)]:

A-O—CO—X—CO—O-A  (7)

(wherein A represents a 2,2,6,6-tetramethylpiperidine-1-oxyl-4-yl group, X represents a single bond, an alkylene group having 1 to 12 carbon atoms, a phenylene group that can have a substitutent, a naphthylene group that can have a substituent, a divalent group represented by the formula:

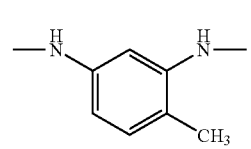

or a divalent group represented by the formula:

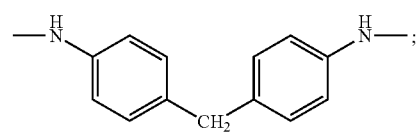

a compound represented by formula (8) [hereinafter referred to as compound (8)]:

(wherein $R^4$, $R^5$, $R^6$ and $R^7$ are respectively the same or different and represent a 2,2,6,6-tetramethylpiperidine-1-oxyl-4-yl group or an alkyl group and at least two of these are 2,2,6,6-tetramethylpiperidine-1-oxyl-4-yl groups); a compound represented by formula (9) [hereinafter referred to as compound (9)]:

(9)

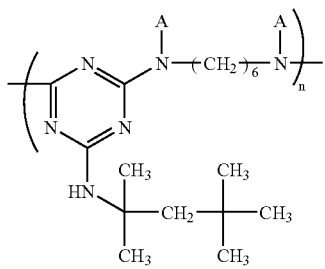

(wherein A is the same as above and n is an integer of 1 to 10); a compound represented by formula (10) [hereinafter referred to as compound (10)]:

(10)

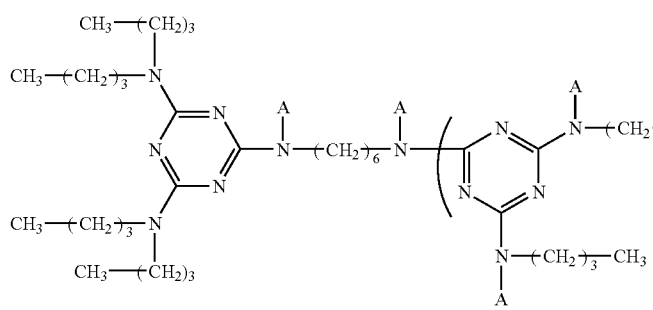

(wherein A is the same as above and p is an integer of 1 to 10); a compound represented by formula (11) [hereinafter referred to as compound (11)]:

(11)

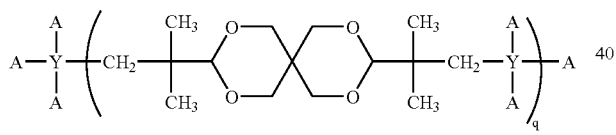

(wherein A is the same as above, Y is a quadrivalent group represented by the formula:

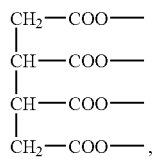

q represents an integer of 1 to 10; a compound represented by formula (12) [hereinafter referred to as compound (12)]:

(12)

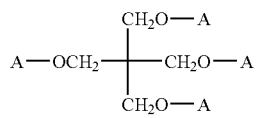

(wherein A is the same as above); a compound represented by formula (13) [hereinafter referred to as compound (13)]:

(13)

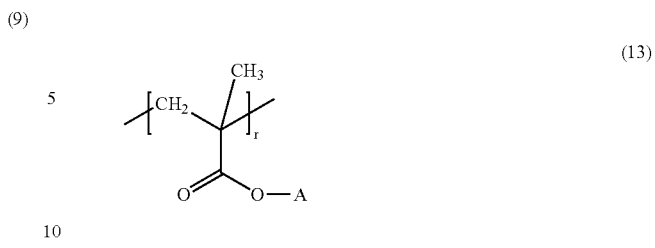

(wherein A is the same as above and r is an integer of 10 to 1000); a compound represented by formula (14) [hereinafter referred to as compound (14)]:

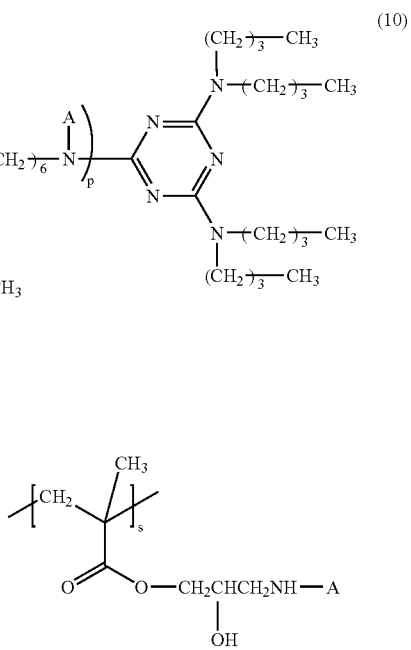

(wherein A is the same as above and s is an integer of 2 to 1000); and a compound represented by formula (15) [hereinafter referred to as compound (15)]:

(15)

(wherein A is the same as above and t is an integer of 2 to 1000). Compounds 10, 12, 14 and 15 are novel compounds.

In compound (7), examples of the alkylene group represented by X in formula (7) are linear or branched alkylene groups having 1 to 12 carbon atoms, preferably linear or branched alkylene groups having 2 to 8 carbon atoms such as an ethylene group, a propylene group, a trimethylene group, a tetramethylene group, a hexamethylene group and an octamethylene group. A specific example of compound (7) wherein X in formula (7) is an alkylene group is a compound wherein X is an octamethylene group. This compound can be prepared by oxidizing ADK STAB LA-77 (trade name, available from Asahi Denka Co., Ltd.) by a known method for preparing imine-N-oxyl from imine.

In compound (8), examples of the alkyl group represented by $R^4$, $R^5$, $R^6$ and $R^7$ in formula (8) are linear or branched alkyl groups having 1 to 15 carbon atoms, preferably a tridecyl group. A specific example of compound (8) is a compound wherein all of $R^4$, $R^5$, $R^6$ and $R^7$ in formula (8) are 2,2,6,6-tetramethylpiperidine-1-oxyl-4-yl groups. This compound can be prepared by oxidizing ADK STAB LA-57 (trade name, available from Asahi Denka Co., Ltd.) by a known method for preparing imine-N-oxyl from imine.

In compound (9), n in formula (9) is an integer of 1 to 10, preferably an integer of 3 to 5. A specific example of compound (9) is a compound in which n in formula (9) is 3 to 5, which can be prepared by oxidizing Chimassorb 944LD (trade name, available from Ciba Specialty Chemicals) by a known method for preparing imine-N-oxyl from imine.

In compound (10), p in formula (10) is an integer of 1 to 10, preferably an integer of 2 to 4. A specific example of compound (10) is a compound in which p in formula (10) is 2 to 4, which can be prepared by oxidizing Chimassorb 2020FDL (trade name, available from Ciba Specialty Chemicals) by a known method for preparing imine-N-oxyl from imine. The preparation method is described below in more detail.

Compound (10) can be prepared by reacting a triazine derivative represented by formula (16) [hereinafter referred to as compound (16)]:

The amount of the solvent is not particularly limited but is usually 10 to 10000 parts by weight, preferably 100 to 2000 parts by weight, based on 100 parts by weight of compound (16).

As the peroxide, both hydrogen peroxide and organic peroxides such as hydroperoxide and peracids can be used, but from the viewpoints of economic efficiency and reducing the amount of waste material, hydrogen peroxide is preferable. When using hydrogen peroxide, usually, a 5 to 70% by weight aqueous solution, preferably a 20 to 50% by weight aqueous solution, is used. The amount of the peroxide is 1.5 to 50 mol, preferably 1.5 to 10 mol, based on 1 mol of the 2,2,6,6-tetramethylpiperidine-4-yl group.

When reacting, reaction can be conducted in the presence of an organic compound having a cyano group as an additive. The amount of the additive is usually 10 to 10000 parts by weight, preferably 100 to 500 parts by weight, based on 100 parts by weight of compound (16). The organic compound having a cyano group is not particularly limited, excluding compounds having a polymerizable unsaturated bond in the molecule such as acrylonitrile, and preferable examples are aliphatic nitriles such as acetonitrile, propionitrile, butyronitrile, valeronitrile and capronitrile and aromatic nitriles such as benzonitrile and tolunitrile. Also, when using an aqueous solution of hydrogen peroxide as the peroxide, the organic compound having a cyano group is preferably an aqueous compound and particularly preferably is acetonitrile and/or propionitrile.

A catalyst can also be used. Examples of the catalyst are catalysts that are used in the known method of oxidizing a

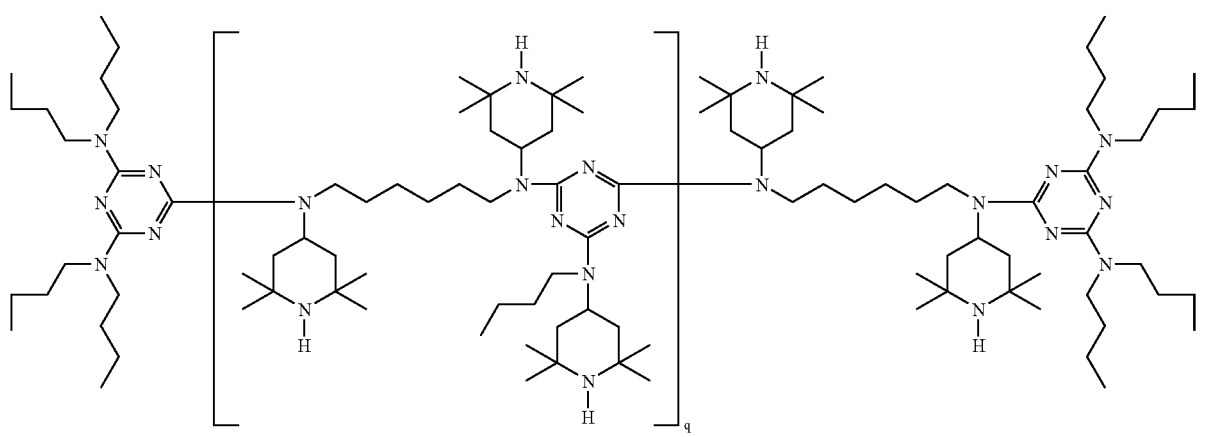

(16)

with a peroxide.

The solvent is at least one solvent selected from an aromatic hydrocarbon, an aliphatic hydrocarbon, an alicyclic hydrocarbon and an ether solvent or a mixture thereof. Examples of the aromatic hydrocarbon are benzene, toluene and xylene, examples of the aliphatic hydrocarbon are n-hexane, n-heptane and n-octane, examples of the alicyclic hydrocarbon are cyclohexane, cyclooctane and cycloheptane and examples of the ether solvent are diethyl ether, diisopropyl ether and tetrahydrofurane, but the solvent is not limited to these. A solvent that dissolves compound (16) (for example tetrahydrofuran) is preferable.

secondary amine having steric hindrance with a peroxide to prepare the corresponding compound having a nitroxide free radical. Preferable catalysts are compounds containing a metal atom selected from group 6 of the 18-group periodic table such as tungsten and molybdenum. Examples of the tungsten compound are tungstic acid, phosphotungstic acid, paratungstic acid, and alkali metal salts (sodium salt and potassium salt) and ammonium salts thereof. Examples of the molybdenum compound are molybdic acid, molybdenum oxide, molybdenum carbonyl, and alkali metal salts (sodium salt and potassium salt) and ammonium salts thereof. Specific examples are ammonium paratungstate, sodium tungstate, phosphotungstic acid, sodium molybdate, molybdenum trioxide and molybdenum hexacarbonyl.

The amount of the catalyst is usually 0.01 to 100 parts by weight, preferably 1 to 10 parts by weight, based on 100 parts by weight of compound (16).

When preparing compound (10), first, compound (16), the solvent, the additive and catalyst are placed in a reaction vessel and while stirring, the peroxide is dropped. The reaction temperature is at most the boiling point of the compound used in the present invention and is preferably 20 to 70° C. The reaction time is influenced by the reaction temperature, the additive and the catalyst, but is usually about 1 to 48 hours. After the completion of the reaction, the reaction solution is dropped in a poor solvent such as water and the precipitated crystal is separated by filtration, washed and dried under reduced pressure to isolate the target substance.

In compound (11), q in formula (11) is an integer of 1 to 10, preferably an integer of 1 to 2. A specific example of compound (11) is a compound in which q in formula (11) is 1 to 2, which can be prepared by oxidizing ADK STAB LA-68 (trade name, available from Asahi Denka Co., Ltd.) by a known method for preparing imine-N-oxyl from imine.

Compound (12) can be prepared by reacting 2,2-bis(benzenesulfonyloxymethyl)-1,3-propanediol dibenzenesulfonate, which is obtained by reacting pentaerythritol and benzenesulfonyl chloride, with alkali metal salt of 4-hydroxy-2,2,6,6-tetramethylpiperidine-1-oxyl. The preparation method is described below in more detail.

A solvent can be used for reaction of pentaerythritol and benzenesulfonyl chloride. The solvent can be at least one solvent selected from an aromatic hydrocarbon, an aliphatic hydrocarbon, an alicyclic hydrocarbon, a sulfur-containing organic compound and a nitrogen-containing organic compound or a mixture thereof, as long as the solvent does not react with benzenesulfonyl chloride. Examples of the aromatic hydrocarbon are benzene, toluene and xylene, examples of the aliphatic hydrocarbon are n-hexane, n-heptane and n-octane and examples of the alicyclic hydrocarbon are cyclohexane, cyclooctane and cycloheptane. Examples of the nitrogen-containing organic compound are pyridine and dimethyl formamide and examples of the sulfur-containing organic compound are dimethyl sulfoxide, but are not limited thereto. A solvent (such as pyridine), which can be used for dissolving pentaerythritol and is subjected to dehydration treatment by a known method, is preferable. The amount of the solvent is not particularly limited but is usually 10 to 10000 parts by weight, preferably 100 to 2000 parts by weight, based on 100 parts by weight of pentaerythritol.

To prepare 2,2-bis(benzenesulfonyloxymethyl)-1,3-propanediol dibenzenesulfonate, first, pentaerythritol and the solvent are placed in a reaction vessel in the presence of an inert gas and while stirring, benzenesulfonyl chloride is dropped. The reaction temperature is not particularly limited and is at most the boiling point of the compound used in the present invention, preferably 0 to 50° C. The reaction time is influenced by the reaction temperature, but is usually about 10 minutes to 10 hours. After completion of the reaction, the precipitated crystal is separated by filtration and recrystallized to isolate the target substance.

A solvent can be used for reaction of 2,2-bis(benzenesulfonyloxymethyl)-1,3-propanediol dibenzenesulfonate and alkali metal salt of 4-hydroxy-2,2,6,6-tetramethylpiperidine-1-oxyl. The solvent can be at least one solvent selected from an aromatic hydrocarbon, an aliphatic hydrocarbon, an alicyclic hydrocarbon, a sulfur-containing organic compound and a nitrogen-containing organic compound or a mixture thereof, as long as the solvent does not react with sodium hydride. Examples of the aromatic hydrocarbon are benzene, toluene and xylene, examples of the aliphatic hydrocarbon are n-hexane, n-heptane and n-octane and examples of the alicyclic hydrocarbon are cyclohexane, cyclooctane and cycloheptane. Examples of the nitrogen-containing organic compound are pyridine and dimethyl formamide and examples of the sulfur-containing organic compound are dimethyl sulfoxide, but are not limited thereto. Preferably, the solvent is subjected to dehydration treatment by a known method. The amount of the solvent is not particularly limited but is usually 10 to 50000 parts by weight, preferably 100 to 5000 parts by weight, based on 100 parts by weight of 2,2-bis(benzenesulfonyloxymethyl)-1,3-propanediol dibenzenesulfonate. To prepare salt of 4-hydroxy-2,2,6,6-tetramethylpiperidine-1-oxyl, a base is used. As the base, sodium, potassium, lithium, sodium hydride and t-butoxy potassium can be used and sodium hydride is preferable. Commercially available products of sodium hydride can be used as they are without washing the oil content, but preferably those washed with n-hexane are used. The amount of the base is usually 1 to 30 mol, preferably 1 to 3 mol, based on 1 mol of 4-hydroxy-2,2,6,6-tetramethylpiperidine-1-oxyl.

To prepare compound (12), first, the base and the solvent are placed in a reaction vessel in the presence of an inert gas and while stirring, 4-hydroxy-2,2,6,6-tetramethylpiperidine-1-oxyl is dropped. The reaction temperature for forming alkali metal salt of 4-hydroxy-2,2,6,6-tetramethylpiperidine-1-oxyl is not particularly limited and is at most the boiling point of the compound used in the present invention, preferably 0 to 50° C. The reaction time is influenced by the reaction temperature, but is usually about 10 minutes to 10 hours.

Thereafter, a 2,2-bis(benzenesulfonyloxymethyl)-1,3-propanediol dibenzenesulfonate solution is dropped to conduct reaction. The reaction temperature is not particularly limited and is at most the boiling point of the compound used in the present invention, preferably 0 to 50° C. The reaction time is influenced by the reaction temperature, but is usually about 10 minutes to 24 hours. After the completion of the reaction, the precipitated crystal is separated by filtration and the filtrate is evaporated to dryness. Then, washing and extracting of the obtained solid is repeated to isolate the target substance.

In compound (13), r in formula (13) is an integer of 10 to 1000, preferably an integer of 10 to 100. Compound (13) can be prepared by oxidizing an oligomer and or polymer obtained by polymerizing ADK STAB LA-87 (trade name, available from Asahi Denka Co., Ltd.) by a known method for preparing imine-N-oxyl from imine.

In compound (14), s in formula (14) is an integer of 2 to 1000, preferably an integer of 10 to 200. Compound (14) can be prepared by reacting an oligomer and or polymer obtained by polymerizing glycidyl methacrylate with 4-amino-2,2,6,6-tetramethylpiperidine-1-oxyl. The preparation method is described below in more detail.

The oligomer and or polymer of glycidyl methacrylate are obtained by polymerizing glycidyl methacrylate in the presence of a polymerization initiator. The solvent when polymerizing can be at least one solvent selected from an aromatic hydrocarbon, an aliphatic hydrocarbon, an alicyclic hydrocarbon, an aliphatic ketone, a sulfur-containing organic compound and a nitrogen-containing organic compound or a mixture thereof. Examples of the aromatic hydrocarbon are benzene, toluene and xylene, examples of the aliphatic hydrocarbon are n-hexane, n-heptane and n-octane and examples of the alicyclic hydrocarbon are cyclohexane, cyclooctane and cycloheptane. Examples of the aliphatic ketone are acetone, methyl ethyl ketone, methyl propyl ketone, isopropyl methyl ketone, butyl methyl ketone, isobutyl methyl ketone, diethyl ketone, dipropyl ketone, diisopropyl ketone, dibutyl ketone and diisobutyl ketone. Examples of the nitrogen-containing organic compound are pyridine, dimethyl formamide and N-methyl pyrrolidone and examples of the sulfur-containing organic compound are dimethyl sulfoxide, but are not limited thereto. The amount of the solvent is not particularly limited but is usually 10 to 10000 parts by weight, preferably 100 to 1000 parts by weight, based on 100 parts by weight of the monomer.

The polymerization initiator that can be used is an initiator that dissolves in the solvent used for polymerization and examples are conventionally known polymerization initiators such as azo polymerization initiators including 2,2'-azobisisobutyronitrile, 2,2'-azobis-2-methylbutyronitrile and 2,2'-azobis-2,4-dimethylvaleronitrile and organic peroxide polymerization initiators including benzoyl peroxide, lauryl peroxide and bis(4-t-butylcyclohexyl)peroxydicarbonate. The amount of the polymerization initiator is usually 0.01 to 50 parts by weight, preferably 0.1 to 10 parts by weight, based on 100 parts by weight of the monomer.

To prepare the glycidyl methacrylate oligomer and or polymer, first, glycidyl methacrylate, the solvent and the polymerization initiator are placed in a reaction vessel in the presence of an inert gas and then, stirred. The reaction temperature is not particularly limited and is at most the boiling point of the compound used in the present invention. The reaction time is influenced by the amount of the polymerization initiator and the reaction temperature, but is usually about 10 minutes to 24 hours. After completion of the reaction, the precipitated crystal is separated by filtration, washed and dried under reduced pressure to isolate the target substance.

The solvent when reacting the glycidyl methacrylate oligomer and or polymer with the 4-amino-2,2,6,6-tetramethylpiperidine-1-oxyl compound can be at least one solvent that does not react with the amino group selected from an aromatic hydrocarbon, an aliphatic hydrocarbon, an alicyclic hydrocarbon, a sulfur-containing organic compound and a nitrogen-containing organic compound or a mixture thereof. A solvent in which the glycidyl methacrylate oligomer and or polymer and 4-amino-2,2,6,6-tetramethylpiperidine-1-oxyl dissolve (such as N,N-dimethylformamide and cyclohexane) is preferable.

The amount of 4-amino-2,2,6,6-tetramethylpiperidine-1-oxyl is usually 1 to 20 mol, preferably 1 to 3 mol, based on 1 mol of glycidyl methacrylate.

To prepare compound (14), first, the glycidyl methacrylate polymer, the solvent and 4-amino-2,2,6,6-tetramethylpiperidine-1-oxyl are placed in a reaction vessel in the presence of an inert gas and then, stirred. The reaction temperature is a temperature that is lower than the boiling point of the compound used in the present invention and is preferably 50 to 100° C. The reaction time is influenced by the reaction temperature and the amount of 4-amino-2,2,6,6-tetramethylpiperidine-1-oxyl, but is usually about 1 to 48 hours. After the completion of the reaction, the precipitated crystal is separated by filtration, washed and dried under reduced pressure to isolate the target substance.

In compound (15), t in formula (15) is an integer of 2 to 1000, preferably an integer of 10 to 100. Compound (15) can be prepared by reacting an oligomer and or polymer obtained by polymerizing 2-isocyanatoethyl methacrylate with 4-hydroxy-2,2,6,6-tetramethylpiperidine-1-oxyl. The preparation method is described below in more detail.

The oligomer and or polymer of 2-isocyanatoethyl methacrylate are obtained by polymerizing 2-isocyanatoethyl methacrylate in the presence of a polymerization initiator.

The solvent when polymerizing can be at least one solvent selected from an aromatic hydrocarbon, an aliphatic hydrocarbon, an alicyclic hydrocarbon, an aliphatic ketone, a sulfur-containing organic compounds and a nitrogen-containing organic compound or a mixture thereof. Examples of the aromatic hydrocarbon are benzene, toluene and xylene, examples of the aliphatic hydrocarbon are n-hexane, n-heptane and n-octane and examples of the alicyclic hydrocarbon are cyclohexane, cyclooctane and cycloheptane. Examples of the aliphatic ketone are acetone, methyl ethyl ketone, methyl propyl ketone, isopropyl methyl ketone, butyl methyl ketone, isobutyl methyl ketone, diethyl ketone, dipropyl ketone, diisopropyl ketone, dibutyl ketone and diisobutyl ketone. Examples of the nitrogen-containing organic compound are pyridine, dimethyl formamide and N-methyl pyrrolidone and examples of the sulfur-containing organic compound are dimethyl sulfoxide, but are not limited thereto. The amount of the solvent is not particularly limited but is usually 10 to 10000 parts by weight, preferably 100 to 1000 parts by weight, based on 100 parts by weight of the monomer.

The polymerization initiator that can be used is an initiator that dissolves in the solvent used for polymerization and examples are conventionally known polymerization initiators such as azo polymerization initiators including 2,2'-azobisisobutyronitrile, 2,2'-azobis-2-methylbutyronitrile and 2,2'-azobis-2,4-dimethylvaleronitrile and organic peroxide polymerization initiators including benzoyl peroxide, lauryl peroxide and bis(4-t-butylcyclohexyl)peroxydicarbonate. The amount of the polymerization initiator is usually 0.01 to 50 parts by weight, preferably 0.1 to 10 parts by weight, based on 100 parts by weight of the monomer.

To prepare the 2-isocyanatoethyl methacrylate oligomer and or polymer, first, 2-isocyanatoethyl methacrylate, the solvent and the polymerization initiator are placed in a reaction vessel in the presence of an inert gas and then, stirred. The reaction temperature is not particularly limited and is at most the boiling point of the compound used in the present invention. The reaction time is influenced by the amount of the polymerization initiator and the reaction temperature, but is usually about 10 minutes to 24 hours. After the completion of the reaction, the precipitated crystal is separated by filtration, washed and dried under reduced pressure to isolate the target substance.

The solvent when reacting the 2-isocyanatoethyl methacrylate oligomer and or polymer with the 4-hydroxy-2,2,6,6-tetramethylpiperidine-1-oxyl compound can be at least one solvent selected from an aromatic hydrocarbon, an aliphatic hydrocarbon, an alicyclic hydrocarbon, an aliphatic ketone, a sulfur-containing organic compound and a nitrogen-containing organic compound or a mixture thereof. A solvent in which the 2-isocyanatoethyl methacrylate polymer and 4-hydroxy-2,2,6,6-tetramethylpiperidine-1-oxyl dissolve (such as N,N-dimethylformamide) is preferable.

The amount of 4-hydroxy-2,2,6,6-tetramethylpiperidine-1-oxyl is usually 1 to 20 mol, preferably 1 to 5 mol, based on 1 mol of 2-isocyanatoethyl methacrylate. Also, as an additive that accelerates the reaction, tertiary amine (such as triethyl amine, tri-n-butylamine and 4-dimethylaminopyridine) can be used optionally.

To prepare compound (15), first, the 2-isocyanatoethyl methacrylate polymer, the solvent, the additive and 4-hydroxy-2,2,6,6-tetramethylpiperidine-1-oxyl are placed in a reaction vessel in the presence of an inert gas and then, stirred. The reaction temperature is a temperature lower than the boiling point of the compound used in the present invention and is preferably 50 to 100° C. The reaction time is influenced by the reaction temperature, the amount of the additive and the amount of 4-hydroxy-2,2,6,6-tetramethylpiperidine-1-oxyl, but is usually about 1 to 48 hours. After the completion of the reaction, the precipitated crystal is separated by filtration, washed and dried under reduced pressure to isolate the target substance.

The amount of the 2,2,6,6-tetramethylpiperidine-1-oxyl derivative used in the oxidization reaction of the present invention is usually 0.001 to 1 mol, preferably 0.01 to 0.1 mol, based on 1 mol of the heterocyclic alcohol, converted to the 2,2,6,6-tetramethylpiperidine-1-oxyl-4-yl groups in the molecule of the 2,2,6,6-tetramethylpiperidine-1-oxyl derivative.

Examples of the hypohalogenous acid salt used in the oxidization reaction of the present invention are hypochlorite and hypobromite of alkali metals such as lithium, sodium and potassium and alkali earth metals such as calcium. Alkali hypochlorite is preferable and sodium hypochlorite is particularly preferable. The hypohalogenous acid salt is usually added to the reaction system as an aqueous solution. The amount of the hypohalogenous acid salt is within the range of 0.5 to 10 mol, preferably 1 to 1.5 mol, based on 1 mol of the hydroxymethyl group of the heterocyclic alcohol.

The oxidization reaction of the present invention is conducted in the presence of a base. Preferable examples of the base are hydroxides, carbonates and hydrogen carbonates of alkali metals or alkali earth metals and particularly, hydrogen carbonates of alkali metals are preferable. The base is preferably used so that the pH of the aqueous solution of the reaction system becomes 8 to 12, preferably 9 to 10.

In the oxidization reaction of the present invention, a solvent is usually used. As the solvent, water and a mixed solvent of water and a hydrophobic organic solvent can be used. Examples of the hydrophobic organic solvent are a halogenated hydrocarbon such as methylene chloride, dichloroethane, chloroform, and carbon tetrachloride, an aromatic hydrocarbon such as benzene, toluene, xylene and mesitylene, an aliphatic hydrocarbon such as n-hexane and cyclohexane, an ether such as ethyl ether, isopropyl ether and tert-butyl methyl ether and a fatty acid ester such as ethyl acetate. The amount of the solvent is not particularly limited but is preferably 1 to 15 parts by weight based on 1 part by weight of the heterocyclic alcohol.

When only water is used as the solvent in the oxidization reaction of the present invention, the method of using the 2,2,6,6-tetramethylpiperidine-1-oxyl derivative of compounds (7) to (15) is particularly preferable, as the 2,2,6,6-tetramethylpiperidine-1-oxyl derivative can easily be recovered by filtration from the reaction mixture after the completion of the reaction and be reused in the oxidization reaction of the present invention.

Also, in the present invention, a compound that becomes a bromine ion source can be added to the reaction system in order to accelerate the reaction. Examples are alkali bromide metal salts such as potassium bromide and sodium bromide and quaternary ammonium salts such as tetrabutyl ammonium bromide and tetrabutyl ammonium chloride. The amount of these alkali bromide metal salts is 0.05 to 0.5 equivalent, preferably 0.1 to 0.2 equivalent, based on the heterocyclic alcohol. Also, the amount of the quaternary ammonium salt is 0.001 to 0.5 part by weight, preferably 0.01 to 0.1 part by weight, based on 1 part by weight of the heterocyclic alcohol.

Examples of the method for conducting the oxidization reaction of the present invention are the method of reacting by dropping and mixing a hypohalogenous acid salt, preferably as an aqueous solution, in a mixture of a heterocyclic alcohol, the 2,2,6,6-tetramethylpiperidine-1-oxyl derivative of the present invention, a base and a solvent while stirring and the method of reacting by simultaneously dropping both a heterocyclic alcohol and a hypohalogenous acid salt in a mixture of the 2,2,6,6-tetramethylpiperidine-1-oxyl derivative of the present invention, a base and a solvent while stirring.

An example of a specific embodiment of the oxidization reaction is described below.

While holding at −10 to 50° C., preferably 0 to 20° C., a mixture of the 2,2,6,6-tetramethylpiperidine-1-oxyl derivative of the present invention, a heterocyclic alcohol, a base and a solvent is reacted while dropping a hypohalogenous acid salt, preferably an aqueous solution of a hypohalogenous acid salt, thereto over 0.5 to 24 hours. After dropping, the same temperature is maintained for 0.5 to 10 hours to complete the reaction. By reacting in this way, by-production of heterocyclic carboxylic acid can be inhibited and heterocyclic aldehyde can be produced with high selectivity and high yield.

To isolate the heterocyclic aldehyde from the reaction mixture after the completion of the reaction, extraction of the reaction mixture by toluene can be conducted and thereafter, the desired heterocyclic aldehyde can be obtained by distillation.

Hereinafter, the present invention is described in more detail by means of Examples, but the present invention is not limited thereto.

REFERENCE EXAMPLE 1

Preparation of Compound (9)

100.0 g (0.17 mol) of Chimassorb 944LD (trade name, available from Ciba Specialty Chemicals, molecular weight 2000 to 3100), 300.0 g of tetrahydrofuran and 200.0 g of acetonitrile were placed in a 1000 ml reaction vessel and heated to 50° C. Then, 100.0 g (1.03 mol) of 35% hydrogen peroxide was dropped over 1 hour and reaction was conducted for 15 hours at 50 to 55° C. Thereafter, 33.3 g (0.34 mol) of 35% hydrogen peroxide was dropped over 20 minutes and reaction was conducted for 12 hours. The reaction solution obtained in this way was dropped in 1450.0 g of 5° C. water and the precipitate was separated by filtration. The obtained precipitate was washed with acetonitrile and dried to obtain 88.1 g of a 2,2,6,6-tetramethylpiperidine-1-oxyl derivative wherein oxy radical is introduced into the nitrogen atom of the 2,2,6,6-tetramethyl-4-piperidyl group of Chimassorb 944LD, that is the compound of compound (9) wherein n=3 to 5 (hereinafter referred to as PIPO). The oxy radicalization ratio of the obtained PIPO was 84.5% by titration analysis.

REFERENCE EXAMPLE 2

Preparation of Glycidyl Methacrylate Polymer 12.0 g (84 mmol) of glycidyl methacrylate, 48.0 g of toluene and 0.06 g of α,α'-azobisisobutyronitrile were placed in a 100 ml reaction vessel and reaction was conducted for 8 hours at a temperature of 80° C. in a nitrogen atmosphere. After the completion of the reaction, the precipitated crystal was separated by filtration, washed and dried under reduced pressure to obtain 11.2 g of glycidyl methacrylate polymer (yield: 93.5% [based on glycidyl methacrylate], average molecular weight 22500).

REFERENCE EXAMPLE 3

Preparation of Compound (14)

2.00 g (14 mmol) of the glycidyl methacrylate polymer obtained in Reference Example 2, 2.41 g (14 mmol) of 4-amino-2,2,6,6-tetramethylpiperidine-1-oxyl and 6.62 g of N,N-dimethylformamide were placed in a 20 ml reaction vessel and reaction was conducted for 20 hours at a temperature of 80° C. in a nitrogen atmosphere. After the completion of the reaction, the precipitated crystal was separated by filtration, washed and dried under reduced pressure to obtain 3.78 g of compound (14) (yield: 85.5% [based on glycidyl methacrylate], average molecular weight 49600).

IR(KBr)cm$^{-1}$: 3448, 2978, 2937, 1726, 1664, 1466, 1389, 1363, 1269, 1244, 1178, 1149

The ESR chart of the obtained compound (14) is shown in FIG. 1.

REFERENCE EXAMPLE 4

Preparation of 2-isocyanatoethyl Methacrylate Polymer 15.5 g (100 mmol) of 2-isocyanatoethyl methacrylate, 77.5 g of toluene and 0.16 g of α,α'-azobisisobutyronitrile were placed in a 200 ml reaction vessel and stirring was conducted under reflux for 8 hours in a nitrogen atmosphere. After the completion of the reaction, the mixture was dropped in 200 g of cyclohexane and the precipitated crystal was separated by filtration, washed and dried under reduced pressure to obtain 8.73 g of 2-isocyanatoethyl methacrylate polymer (yield: 56.3% [based on 2-isocyanatoethyl methacrylate]).

REFERENCE EXAMPLE 5

Preparation of Compound (15)

22.32 g (15 mmol) of the 2-isocyanatoethyl methacrylate polymer obtained in Reference Example 4, 7.49 g (44 mmol) of 4-hydroxy-2,2,6,6-tetramethylpiperidine-1-oxyl, 0.72 g (7 mmol) of triethylamine and 69.6 g of N,N-dimethylformamide were placed in a 200 ml reaction vessel and reaction was conducted for 23 hours at a temperature of 80° C. in a nitrogen atmosphere. A solution obtained by concentrating and dissolving by heating the reaction solution in 30.0 g of N,N-dimethylformamide was dropped in 300 g of water and the precipitated crystal was separated by filtration, washed and dried under reduced pressure to obtain 4.21 g of crude compound (15). A solution in which 2.67 g of the obtained crude compound (15) was dissolved by heating in 6.00 g of N,N-dimethylformamide was dropped in 150 g of water and the precipitated crystal was separated by filtration, washed and dried under reduced pressure to obtain 2.00 g of compound (15) (hereinafter referred to as PMOT) (yield: 68.2% [based on 2-isocyantoethyl methacrylate], average molecular weight 9800).

IR(KBr)cm$^{-1}$: 3384, 2976, 2945, 1724, 1533, 1466, 1389, 1363, 1261, 1240, 1176, 1151, 1031

Figure 2:
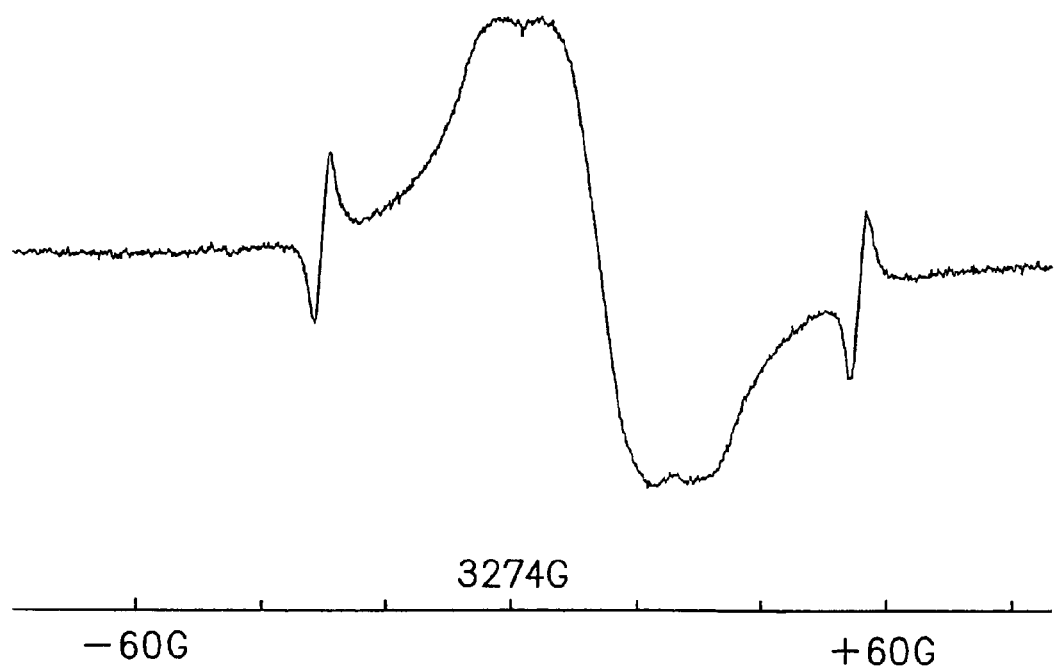
FIG. 2 is an ESR chart of compound (15) obtained in Reference Example 5.

The ESR chart of the obtained compound (15) is shown in FIG. 2.

REFERENCE EXAMPLE 6

Preparation of 2,2-bis(benzenesulfonyloxymethyl)-1,3-propanediol Dibenzenesulfonate 2.27 g (16.7 mmol) of pentaerythritol and 32.6 g of pyridine were placed in a 100 ml reaction vessel and 17.7 g (100 mmol) of benzenesulfonyl chloride was dropped over 0.7 hour while stirring at a temperature of 2 to 4° C. in a nitrogen atmosphere. After dropping, the temperature was raised to 15° C. and reaction was conducted for 4 hours. In a separate 300 ml reaction vessel, the reaction solution was dropped in an 11.3% by weight aqueous solution of hydrochloric acid while stirring at a temperature of 10 to 23° C. After dropping, the water phase was separated. The crystal precipitated by dissolving the oily matter by heating in 48 g of a mixed solution of acetone:methanol (weight ratio 3:1) and then concentrating was separated by filtration, washed and dried under reduced pressure to obtain 9.08 g of 2,2-bis(benzenesulfonyloxymethyl)-1,3-propanediol dibenzenesulfonate (yield: 78.0% [based on pentaerythritol]).

REFERENCE EXAMPLE 7

Preparation of Compound (12)

7.2 g of sodium hydride (60% by weight: 180 mmol) washed with n-hexane in advance and 94.7 g of N,N-dimethylformamide were placed in a 300 ml reaction vessel and a mixed solution containing 10.3 g (60 mmol) of 4-hydroxy-2,2,6,6-tetramethylpiperidine-1-oxyl and 39.5 g of N,N-dimethylformamide was dropped over 1 hour at a temperature of 18 to 24° C. in a nitrogen atmosphere. After dropping, reaction was conducted for 5 hours at room temperature. Thereafter, while stirring at a temperature of at most 5° C., a mixed solution containing 3.48 g (5 mmol) of 2,2-bis(benzenesulfonyloxymethyl)-1,3-propanediol dibenzenesulfonate obtained in Reference Example 6 and 35.0 g of N,N-dimethylformamide was dropped over 0.5 hour. After dropping, reaction was conducted for 20 hours at room temperature. Then, after the precipitated crystal was separated by filtration, the filtrate was evaporated to dryness under reduced pressure to obtain 4.92 g of crude compound (12). Washing of 3.00 g of the crude compound (12) in 30 g of water was repeated. After extracting the residue with toluene, by repeating washing of the oil phase with water and evaporating to dryness, 0.33 g of compound (12) was obtained (yield 14.3% [based on 2,2-bis(benzenesulfonyloxymethyl)-1,3-propanediol dibenzenesulfonate]).

IR(KBr)cm$^{-1}$: 2972, 2937, 2870, 1672, 1463, 1375, 1362, 1244, 1176, 1091

Figure 3:
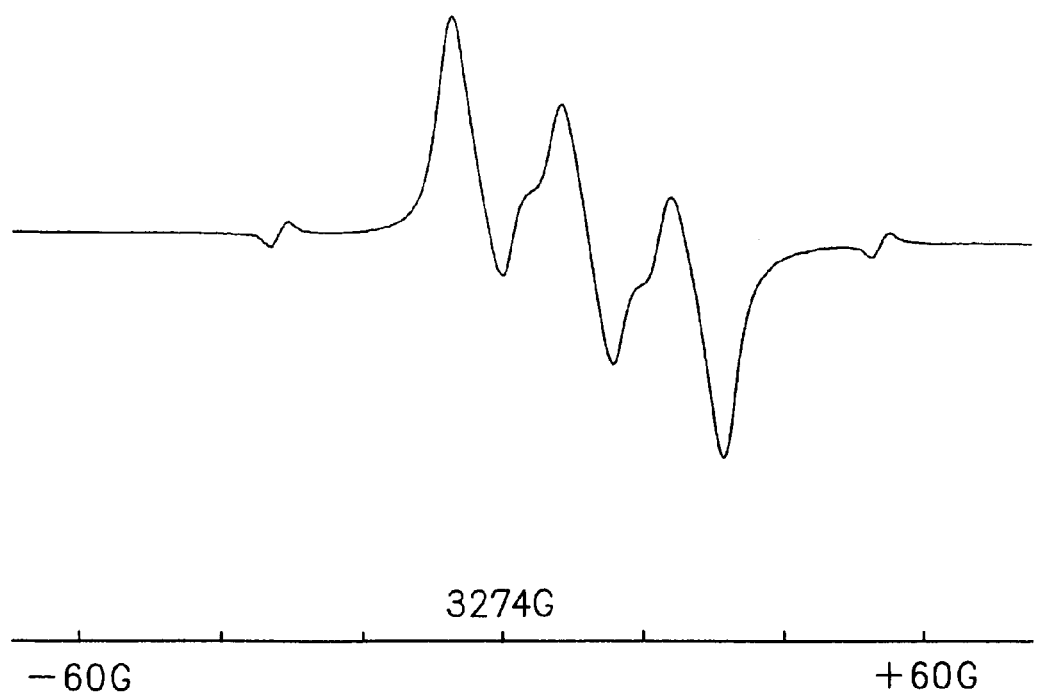
FIG. 3 is an ESR chart of compound (12) obtained in Reference Example 7.

The ESR chart of the obtained compound (12) is shown in FIG. 3.

REFERENCE EXAMPLE 8

Preparation of Compound (10)

10.0 g of Chimassorb 2020FDL (trade name, available from Ciba Specialty Chemicals, molecular weight 2600 to 3400) (piperidyl group when n=3: 35 mmol), 40.0 g of tetrahydrofuran and 20.0 g of acetonitrile were placed in a 200 ml reaction vessel and heated to 50° C. while stirring. Then, 10.0 g (103 mmol) of 35% hydrogen peroxide was dropped over 1 hour and reaction was conducted for 10 hours at 50 to 55° C. Thereafter, 10.0 g (103 mmol) of 35% hydrogen peroxide was added over 1 hour and reaction was conducted for 10 hours. The reaction solution obtained in this way was dropped in 500 g of 5° C. water and the precipitate was separated by filtration. The obtained precipitate was washed with acetonitrile and dried to obtain 9.1 g of a 2,2,6,6-tetramethylpiperidine-1-oxyl derivative, wherein oxy radical is introduced into the nitrogen atom of the 2,2,6,4-tetramethyl-4-piperidyl group of Chimassorb 2020FDL, that is compound (10) wherein p=2 to 4 (hereinafter referred to as 2020NO) (yield 86.1%, p=3). The oxy radicalization ratio of the obtained compound (10) was 82.5% by titration analysis IR(KBr)cm$^{-1}$: 2970, 2933, 2860, 1535, 1473, 1423, 1362, 1313, 1240, 1178, 1113, 1088, 810

Figure 4:
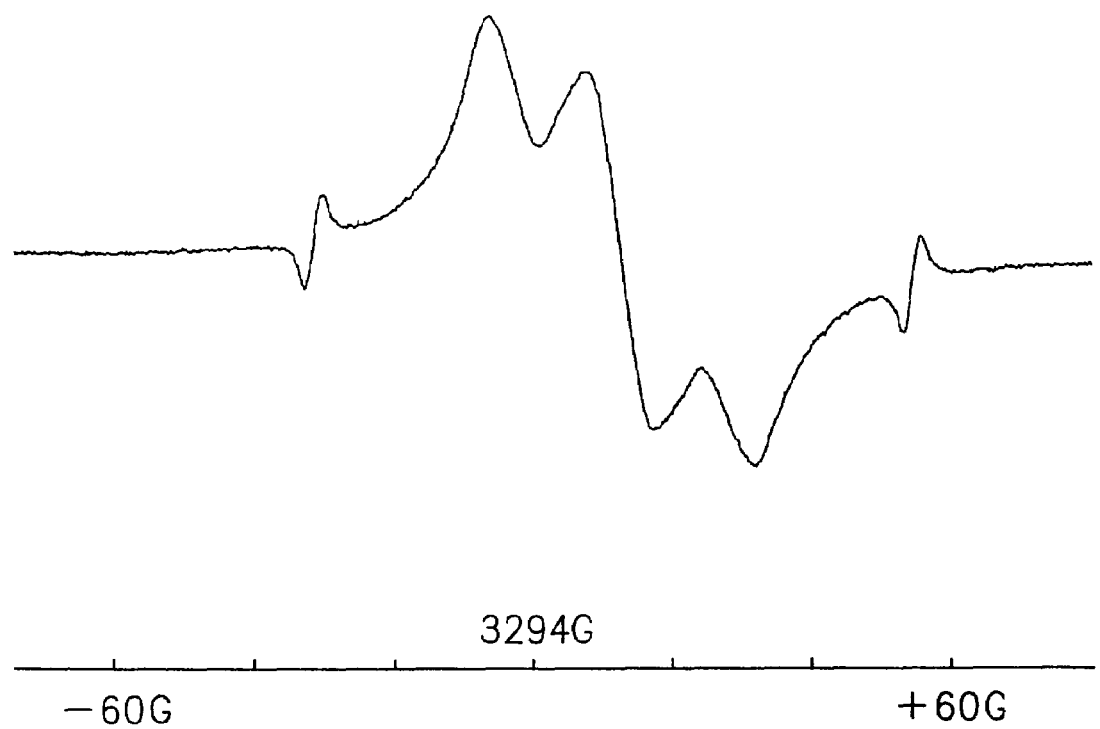
FIG. 4 is an ESR chart of compound (10) obtained in Reference Example 8.

The ESR chart of the obtained compound (10) is shown in FIG. 4.

EXAMPLE 1

5.00 g (0.0458 mol) of 3-pyridinemethanol, 0.144 g of PIPO obtained in Reference Example 1 (2,2,6,6-tetramethylpiperidine-1-oxyl-4-yl group: 0.000458 mol), 10.0 g of toluene and 5.0 g of a 5% by weight aqueous solution of sodium hydrogen carbonate (sodium hydrogen carbonate: 0.0030 mol) were placed in a 100 ml reaction vessel. Then, with maintaining the temperature at 15 to 20° C., reaction was conducted while 28.7 g of an 11.9% by weight aqueous solution of sodium hypochlorite (sodium hypochlorite: 0.0458 mol) was dropped over 4 hours by a microsyringe pump under stirring. Stirring was conducted for another 0.5 hour to complete the reaction. The reaction mixture after the reaction was completed was separated into the organic phase and the water phase and each phase was analyzed by liquid chromatography. By the reaction, 3-pyridinecarbaldehyde was produced with yield of 90.1% (based on 3-pyridinemethanol). As a by-product, 3.4% (based on 3-pyridinemethanol) of nicotinic acid was produced.

EXAMPLE 2

The experiment was conducted in the same manner as in Example 1, except that 0.136 g of 2020NO obtained in Reference Example 8 (2,2,6,6-tetramethylpiperidine-1-oxyl-4-yl group: 0.000458 mol) was used instead of PIPO. As a result, by the reaction, 3-pyridinecarbaldehyde was produced with yield of 87.7% (based on 3-pyridinemethanol). As a by-product, 3.5% (based on 3-pyridinemethanol) of nicotinic acid was produced.

EXAMPLE 3

The experiment was conducted in the same manner as in Example 1, except that 0.150 g of PMOT obtained in Reference Example 5 (2,2,6,6-tetramethylpiperidine-1-oxyl-4-yl group: 0.000458 mol) was used instead of PIPO and 10.0 g of 1,2-dichloroethane was used instead of 10.0 g of toluene. As a result, by the reaction, 3-pyridinecarbaldehyde was produced with yield of 85.3% (based on 3-pyridinemethanol). As a by-product, 5.3% (based on 3-pyridinemethanol) of nicotinic acid was produced.

EXAMPLE 4

The experiment was conducted in the same manner as in Example 1, except that 10.0 g of toluene was not used. After the completion of the reaction, PIPO was separated by filtration and the results of analysis of the reaction filtrate show that 3-pyridinecarbaldehyde was produced with yield of 66.3% (based on 3-pyridinemethanol). As a by-product, 5.0% (based on 3-pyridinemethanol) of nicotinic acid was produced.

EXAMPLE 5

3.00 g (0.0244 mol) of 6-methyl-2-pyridinemethanol, 0.076 g of PIPO obtained in Reference Example 1 (2,2,6,6-tetramethylpiperidine-1-oxyl-4-yl group: 0.000244 mol), 6.0 g of toluene and 3.0 g of a 5% by weight aqueous solution of sodium hydrogen carbonate (sodium hydrogen carbonate: 0.0018 mol) were placed in a 100 ml reaction vessel. Then, with maintaining the temperature at 15 to 20° C., reaction was conducted while 13.5 g of a 13.4% by weight aqueous solution of sodium hypochlorite (sodium hypochlorite: 0.0244 mol) was dropped over 4 hours by a microsyringe pump under stirring. Stirring was conducted for another 0.5 hour to complete the reaction. The reaction mixture after the reaction was completed was separated into the organic phase and the water phase and each phase was analyzed by liquid chromatography. By the reaction, 6-methyl-2-pyridinecarbaldehyde was produced with yield of 94.9% (based on 6-methyl-2-pyridinemethanol). As a by-product, 3.1% (based on 6-methyl-2-pyridinemethanol) of 6-methylpicolinic acid was produced.

EXAMPLE 6

The experiment was conducted in the same manner as in Example 5, except that 0.072 g of 2020NO obtained in Reference Example 8 (2,2,6,6-tetramethylpiperidine-1-oxyl-4-yl group: 0.000244 mol) was used instead of PIPO. As a result, by the reaction, 6-methyl-2-pyridinecarbaldehyde was produced with yield of 93.0% (based on 6-methyl-2-pyridinemethanol). As a by-product, 2.6% (based on 6-methyl-2-pyridinemethanol) of 6-methylpicolinic acid was produced.

EXAMPLE 7

5.00 g (0.0438 mol) of 3-thiophenemethanol, 0.138 g of PIPO obtained in Reference Example 1 (2,2,6,6-tetramethylpiperidine-1-oxyl-4-yl group: 0.000438 mol), 10.0 g of toluene and 5.0 g of a 5% by weight aqueous solution of sodium hydrogen carbonate (sodium hydrogen carbonate: 0.0030 mol) were placed in a 100 ml reaction vessel. Then, with maintaining the temperature at 15 to 20° C., reaction was conducted while 24.4 g of a 13.4% by weight aqueous solution of sodium hypochlorite (sodium hypochlorite: 0.0438 mol) was dropped over 4 hours by a microsyringe pump under stirring. Stirring was conducted for another 0.5 hour to complete the reaction. The reaction mixture after the reaction was completed was separated into the organic phase and the water phase and each phase was analyzed by liquid chromatography. By the reaction, 3-thiophenecarbaldehyde was produced with yield of 87.5% (based on 3-thiophenemethanol). As a by-product, 0.1% (based on 3-thiophenemethanol) of 3-thiophenecarboxylic acid was produced.

COMPARATIVE EXAMPLE 1

The experiment was conducted in the same manner as in Example 1, except that 0.072 g (0.000458 mol) of 2,2,6,6-tetramethylpiperidine-1-oxyl was used instead of PIPO. As a result, by the reaction, 3-pyridinecarbaldehyde was produced with yield of 61.2% (based on 3-pyridinemethanol). As a by-product, 9.2% (based on 3-pyridinemethanol) of nicotinic acid was produced.

COMPARATIVE EXAMPLE 2

The experiment was conducted in the same manner as in Example 5, except that 0.038 g (0.000244 mol) of 2,2,6,6-tetramethylpiperidine-1-oxyl was used instead of PIPO. As a result, by the reaction, 6-methyl-2-pyridinecarbaldehyde was produced with yield of 80.8% (based on 6-methyl-2-pyridinemethanol). As a by-product, 9.0% (based on 6-methyl-2-pyridinemethanol) of 6-methylpicolinic acid was produced.

COMPARATIVE EXAMPLE 3

The experiment was conducted in the same manner as in Example 7, except that 0.072 g (0.000458 mol) of 2,2,6,6-tetramethylpiperidine-1-oxyl was used instead of PIPO. As a result, by the reaction, 3-thiophenecarbaldehyde was produced with yield of 52.3% (based on 3-thiophenemethanol). As a by-product, 2.3% (based on 3-thiophenemethanol) of 3-thiophenecarboxylic acid was produced.

REFERENCE EXAMPLE 9

865 mg (8 mmol) of benzyl alcohol, 25 mg of compound (14) obtained in Reference Example 3 (2,2,6,6-tetramethylpiperidine-1-oxyl-4-yl group: 0.08 mmol), 1.6 cc of a 0.5 normality aqueous solution of potassium bromide and 20 cc of methylene chloride were placed in a 100 ml reaction vessel. Then, with maintaining the temperature at 0 to 2° C., reaction was conducted while 74.48 g (20 mmol) of a 2.0% by weight aqueous solution of sodium hypochlorite (adjusted to pH 8.6 by a 5% by weight aqueous solution of sodium hydrogen carbonate) was dropped over 0.5 hour under stirring and stirring was conducted for another 0.5 hour. The reaction mixture after the reaction was completed was separated into the organic phase and the water phase and each phase was analyzed by liquid chromatography. By the reaction, benzaldehyde was produced with yield of 82.5% (based on benzyl alcohol). As a by-product, 17.5% (based on benzyl alcohol) of benzoic acid was produced.

REFERENCE EXAMPLE 10

The experiment was conducted in the same manner as in Reference Example 9, except that 15 mg of compound (12) obtained in Reference Example 7 (2,2,6,6-tetramethylpiperidine-1-oxyl-4-yl group: 0.08 mmol) was used instead of compound (14) and 37.24 g (10 mmol) of the 2.0% by weight aqueous solution of sodium hypochlorite was used. As a result, by the reaction, benzaldehyde was produced with yield of 78.8% (based on benzyl alcohol).

REFERENCE EXAMPLE 11

The experiment was conducted in the same manner as in Reference Example 9, except that 15 mg (0.08 mmol) of 4-methoxy-2,2,6,6-tetramethylpiperidine-1-oxyl was used instead of compound (14) and 37.24 g (10 mmol) was used instead of 74.48 g (20 mmol) of the 2.0% by weight aqueous solution of sodium hypochlorite. As a result, by the reaction, benzaldehyde was produced with yield of 33.0% (based on benzyl alcohol).

INDUSTRIAL APPLICABILITY

According to the present invention, by reacting in the co-presence of a 2,2,6,6-tetramethylpiperidine-1-oxyl derivative having at least two 2,2,6,6-tetramethylpiperidine-1-oxyl-4-yl groups, heterocyclic aldehyde can be prepared by oxidizing heterocyclic alcohol with high selectivity and high yield.

The invention claimed is:

1. A process for preparing heterocyclic aldehyde, which comprises reacting a heterocyclic compound having at least one hydroxymethyl group bonded to a carbon atom of a heterocyclic ring with a hypohalogenous acid salt in the presence of a base to oxidize said hydroxymethyl group, wherein the reaction is conducted in the co-presence of a 2,2,6,6-tetramethylpiperidine-1-oxyl derivative having at least four 2,2,6,6-tetramethylpiperidine-1-oxyl-4-yl groups, said heterocyclic compound having at least one hydroxymethyl group bonded to a carbon atom of a heterocyclic ring is a pyridinemethanol represented by formula (3):

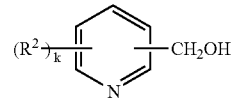

(3)

(wherein $CH_2OH$ and $R^2$ are substituents bonded to a carbon atom of a pyridine ring; $R^2$ represents an alkyl group; k is an integer of 0 to 4) and said heterocyclic aldehyde is a pyridinecarbaldehyde represented by formula (4):

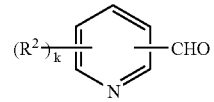

(4)

(wherein $R^2$ and k are the same as above).

2. A process for preparing heterocyclic aldehyde, which comprises reacting a heterocyclic compound having at least one hydroxymethyl group bonded to a carbon atom of a heterocyclic ring with a hypohalogenous acid salt in the presence of a base to oxidize said hydroxymethyl group, wherein the reaction is conducted in the co-presence of a 2,2,6,6-tetramethylpiperidine-1-oxyl derivative having at least two 2,2,6,6-tetramethylpiperidine-1-oxyl-4-yl groups, said heterocyclic compound having at least one hydroxymethyl group bonded to a carbon atom of a heterocyclic ring is a thiophenemethanol represented by formula (5):

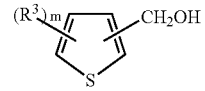

(5)

(wherein $CH_2OH$ and $R^3$ are substituents bonded to a carbon atom of a thiophene ring; $R^3$ represents an alkyl group; m is an integer of 0 to 3) and said heterocyclic aldehyde is a thiophenecarbaldehyde represented by formula (6):

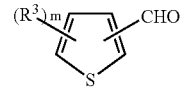

(6)

(wherein $R^3$ and m are the same as above).

* * * * *